(12) United States Patent
Hübinette et al.

(10) Patent No.: US 9,925,145 B2
(45) Date of Patent: Mar. 27, 2018

(54) ORAL DELIVERY PRODUCT

(75) Inventors: Fredrik Hübinette, Uppsala (SE); Thomas Kull, Djursholm (SE); Lars Björkholm, Hellerup (DK)

(73) Assignee: EXCELLENT TECH PRODUCTS I SVERIGE AB, Ulricehamn (SE)

( * ) Notice: Subject to any disclaimer, the term of this patent is extended or adjusted under 35 U.S.C. 154(b) by 507 days.

(21) Appl. No.: 13/255,980

(22) PCT Filed: Mar. 10, 2010

(86) PCT No.: PCT/SE2010/050269
§ 371 (c)(1),
(2), (4) Date: Dec. 5, 2011

(87) PCT Pub. No.: WO2010/104464
PCT Pub. Date: Sep. 16, 2010

(65) Prior Publication Data
US 2012/0128734 A1    May 24, 2012

(30) Foreign Application Priority Data
Mar. 13, 2009 (SE) .................... 0950153

(51) Int. Cl.
*A61K 9/16* (2006.01)
*A61K 31/465* (2006.01)

(52) U.S. Cl.
CPC .......... *A61K 9/1652* (2013.01); *A61K 31/465* (2013.01)

(58) Field of Classification Search
None
See application file for complete search history.

(56) References Cited

U.S. PATENT DOCUMENTS

| | | | |
|---|---|---|---|
| 4,371,516 A | 2/1983 | Gregory | |
| 5,716,337 A * | 2/1998 | McCabe | A61F 13/00021 602/42 |
| 2005/0053665 A1 * | 3/2005 | Ek et al. | 424/488 |
| 2006/0147498 A1 * | 7/2006 | Jonsson et al. | 424/441 |
| 2008/0173317 A1 | 7/2008 | Robinson | |

FOREIGN PATENT DOCUMENTS

| | | |
|---|---|---|
| WO | 2005023227 A2 | 3/2005 |
| WO | 2007036946 A1 | 4/2007 |
| WO | 2007073346 A1 | 6/2007 |
| WO | WO2007/073346 * | 6/2007 |
| WO | 2007104573 A2 | 9/2007 |
| WO | 2010031552 A1 | 3/2010 |

OTHER PUBLICATIONS

Kinam, "Solid dosage forms: powders and granules," Chapter 2, available online as of Jan. 16, 2011; http://kinam.com/Lectures/363/2.%20Powders%20&%20Granules%20Text.pdf.*
Google search results showing Kinam date of Jan. 16, 2011, accessed 2014.*

* cited by examiner

*Primary Examiner* — David J Blanchard
*Assistant Examiner* — Alissa Prosser
(74) *Attorney, Agent, or Firm* — Porter Wright Morris & Arthur LLP

(57) ABSTRACT

An oral delivery product comprising a semi-permeable pouch designed for delivery of an active agent in the oral cavity of a subject. The pouch encloses multiple particles, and the particles are alginate matrices that comprise an active agent, e.g. nicotine. The alginate is e.g. sodium alginate, such as PROTANAL® LFR 5/60 or PROTANAL® LF 10/60.

24 Claims, 3 Drawing Sheets

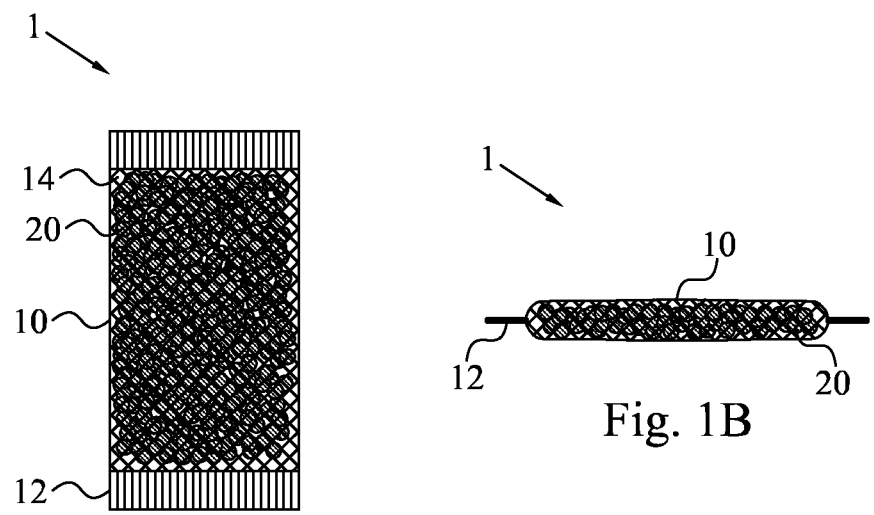
Fig. 1A
Fig. 1B
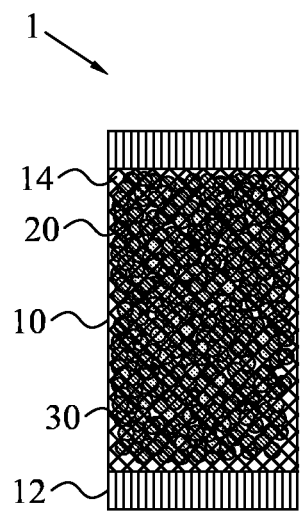
Fig. 2

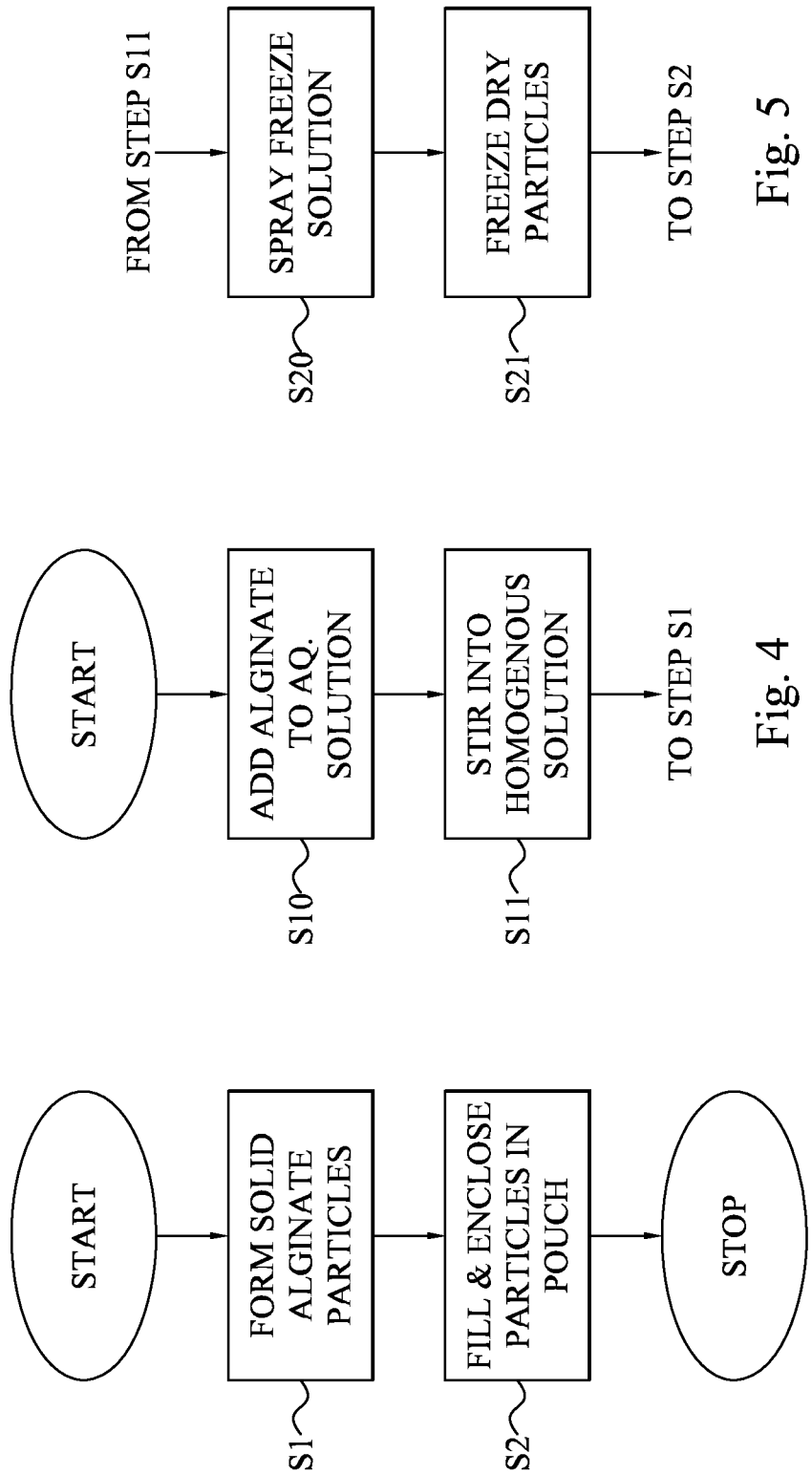

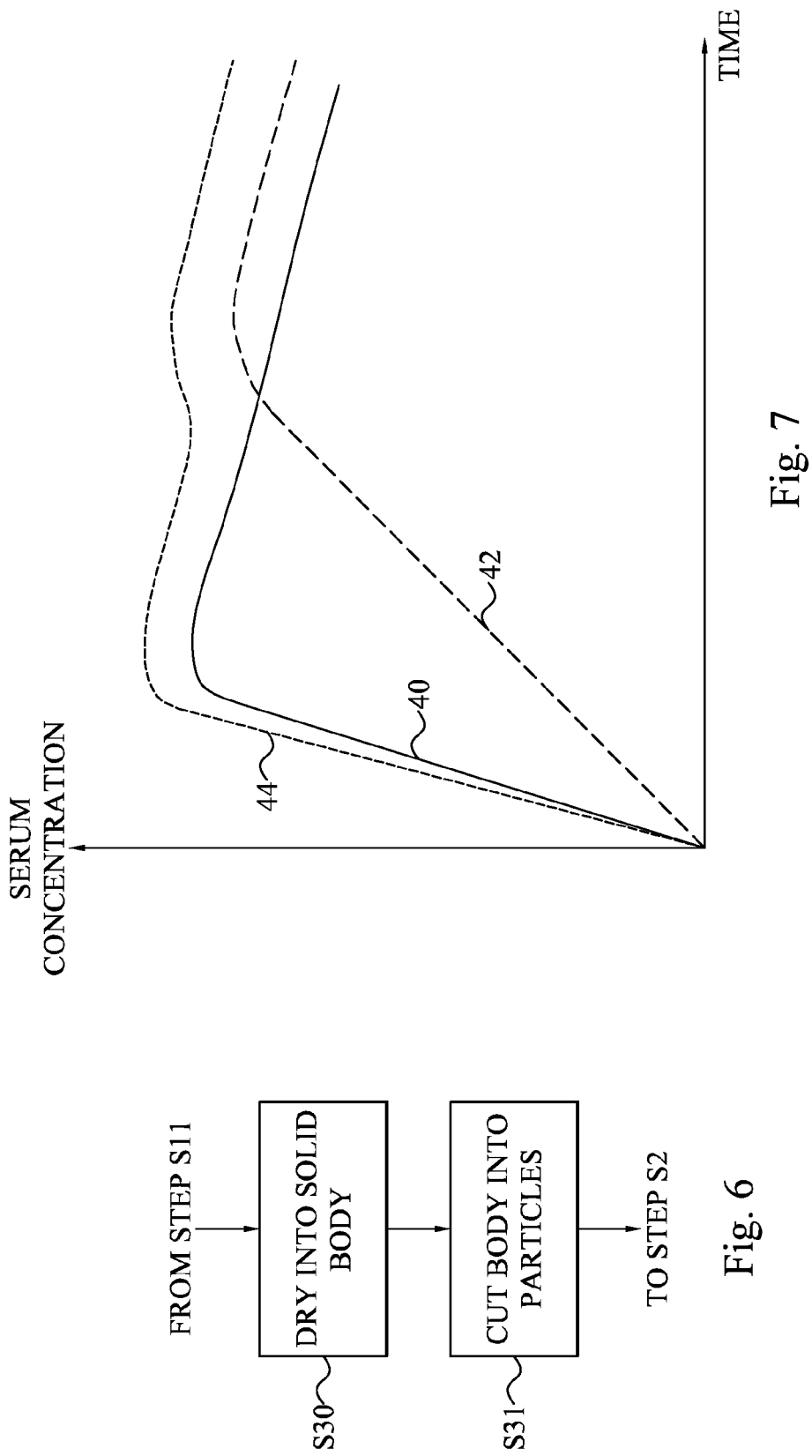

ORAL DELIVERY PRODUCT

RELATED APPLICATION

The present application is a 371 of PCT/SE2010/050269 filed Mar. 10, 2010.

TECHNICAL FIELD

The present invention generally relates to oral delivery of active agents, and in particular to an oral delivery product in the form of an oral pouch.

BACKGROUND

There are many ways of delivering active pharmaceutical agents to a patient body depending on the type of drug and the disorder to treat or prevent. A common administration protocol is oral delivery of oral formulations, such as tablets, capsules and lozenges. In this administration route, the tablet is swallowed for release of the agent in the intestine.

A problem associated with oral delivery to the stomach is that many drugs may be degraded during the passage through the acid environment of the gastrointestinal system. When the agent has entered the intestine it is taken up into the blood stream via the portal vein in the liver, where a large portion of the active agent is typically metabolized into inactive chemicals by the enzymes of the so-called first-pass metabolism.

These factors result in a significant delay before a positive therapeutic effect can be noted, leading to a risk of gastrointestinal side effects augmented by the need of administering considerably higher amount of the active agent than would be needed by, for instance, a direct injection of a drug solution into the vein.

WO 2007/104573 discloses the delivery of the active agent nicotine to the oral cavity of a patient in the form of a snuff product. The snuff product comprises a semi-permeable snuff pouch enclosing small particles of microcrystalline cellulose having the nicotine sorbed to the surface of the cellulose particles. When being placed between the lip and the teeth of the patient, the onset of the nicotine effect is very rapid, typically within 1 to 2 minutes after application of the snuff pouch.

WO 2005/023227 discloses nicotine-containing pharmaceutical compositions wherein nicotine is absorbed into and/or adsorbed onto cellulose of non-seed organism origin, especially cellulose from algae, bacteria and/or fungi. A vast amount of products comprising the pharmaceutical compositions are given in the document, including chewing gums, mouth sprays, nasal sprays, inhaling devices, tablets, lozenges, buccal sachets, transdermal patches and powders.

SUMMARY

The nicotine molecules present on the surface of the cellulose particles are exposed to a potentially harsh environment. For instance, ambient oxygen may oxidize the exposed nicotine into, among others, nicotine-N-oxide. Furthermore, several of the additives suggested in WO 2007/104573 and WO 2005/023227, in particular, color and flavoring agents can be quite reactive, thereby negatively affecting the nicotine bound to the cellulose particle surface.

The present invention overcomes these and other drawbacks of the prior art arrangements.

It is a general objective to provide an efficient oral delivery product.

It is a particular objective according to an embodiment to provide an oral delivery product that can be used as a smoke or snuff curing product.

Briefly, the present invention involves an oral delivery product comprising a semi-permeable pouch designed for being placeable in an oral cavity of a subject, preferably mammalian subject and more preferably a human subject. The pouch is preferably constructed to be placeable under the lip and between the lip and the teeth of a human subject in similarity to a wet snuff pouch or bag.

The semi-permeable pouch encloses and comprises multiple solid particles of at least one alginate salt of monovalent cation. These alginate particles further comprise at least one biologically active substance within the matrix formed by the alginate molecules of the particles.

When being placed in the oral cavity of the subject the moisture naturally present in the mouth causes a gradual dissolution of the alginate particles and a delivery of the at least one biologically active substance entrapped therein. The so released at least one biologically active substance can achieve a local biological, including therapeutic, effect in the oral cavity or, preferably, a system biological effect in the subject by being systemically taken up through the mucous membranes in the mouth.

The semi-permeable pouch can comprise a single alginate salt species achieving a fast or prolonged substance delivery depending on the particular molecular weight and viscosity of the alginate salt. A mixture of different alginate salt species can also be used to achieve a controlled release according to a desired delivery profile by mixing alginate molecules of different molecular weights and viscosities.

The alginate matrix of the multiple solid particles efficiently protects the at least one biologically active substance contained therein during the shelf life of the product. Furthermore, a controlled local environment, added to meet stability requirements, administration requirements and/or effect efficiency of the at least one biologically active substance, can be achieved through the inclusion of selected additives in the alginate matrices.

BRIEF DESCRIPTION OF THE DRAWINGS

The invention together with further objects and advantages thereof, may best be understood by making reference to the following description taken together with the accompanying drawings, in which:

FIGS. 1A and 1B illustrate a view from above and a side view of an embodiment of an oral delivery product;

FIG. 2 illustrates a view from above of another embodiment of an oral delivery product;

FIG. 3 is a flow diagram illustrating a method of producing an oral delivery product according to an embodiment;

FIG. 4 is a flow diagram illustrating additional, optional steps of the producing method in FIG. 3;

FIG. 5 is a flow diagram illustrating an embodiment of the forming step in FIG. 3;

FIG. 6 is a flow diagram illustrating another embodiment of the forming step in FIG. 3; and FIG. 7 is a schematic diagram of serum concentration of an active agent versus time using an embodiment of the oral delivery product.

DETAILED DESCRIPTION

Throughout the drawings, the same reference characters will be used for corresponding or similar elements.

The present embodiments relate to an oral delivery product that can be used for achieving a controlled release of a biologically active substance to an animal, preferably a mammalian and more preferably a human being.

The oral delivery product of the invention is designed for being placed in the oral cavity of the animal, preferably in contact with the mucous membrane of the oral cavity. The product is based on providing multiple solid particles carrying the biologically active substance within a matrix formed by the particles. These matrix-forming particles not only work as a carrier of the active substance but also provide a controlled, local environment within the matrix for the biologically active substance. As a consequence, the oral delivery product can advantageously be used in connection with biologically active substances requiring a certain local environment for achieving its biologically effect, for being efficiently taken up in the animal body and/or protecting the biologically active substance from degradation and other reactive substances that might be present in the oral cavity or indeed in the oral delivery product.

The oral delivery product is based on the usage of at least one alginate salt. Alginate, the salt of alginic acid, is a linear polysaccharide naturally produced by brown seaweeds (Phaeonphyceae, including *Laminaria*). Alginate is composed of multiple monomer residues, typically 100 to 3 000 monomers, linked together in a flexible chain. These residues are mainly of β-(1→4)-linked D-mannuronic acid (M) residues and β-(1→4)-linked L-guluronic acid (G) residues. These two residues are epimers and only differ at C5. In the polymer chain, they though give rise to very different conformations with any two D-mannuronic acid residues being $^4C_1$-diequatorially linked while the link connecting any to L-guluronic acid residues is a $^1C_4$-diaxial link as is illustrated in formula I:

enclose a matrix presenting a substantially isolated environment. This means that the particles are very suitable as carriers for biologically active substances to be administered in a controlled release process and in particular sensitive active substances or substances requiring a certain local environment for achieving an efficient administration and uptake and/or preventing degradation or undesired reactions to the active substances.

The embodiments therefore present solid particles of at least one alginate salt of monovalent cation forming a matrix, in which at least one biologically active substance is contained. These multiple solid particles carrying the biologically active substance or substances are in turn enclosed in a semi-permeable pouch to form the oral delivery product. The oral delivery product is therefore designed to generally be used in a similar way as a traditional snuff bag or pouch in that the delivery product achieves its substance administration by being placed in the oral cavity of a subject. The semi-permeable pouch preferably has an overall size and design for allowing it to be effectively placed in the intended place of the oral cavity, preferably under the lip and between the lip and the teeth of the subject. The actual dimensions of the semi-permeable pouch can non-inventively be determined by the person skilled in the art based on the anatomy of the intended subject animal. Thus, for human subjects, the semi-permeable pouch preferably has a size similar to the snuff pouches and bags that are presently used in the tobacco market today.

The semi-permeable pouch may be of any suitable material, including woven or non-woven fabric, such as cotton, fleece, etc., heat sealable non-woven cellulose or other polymeric materials, such as synthetic, semi-synthetic or natural polymeric material, including hydrophilic or hydrophobic materials. Examples of suitable materials are cellu- Formula I

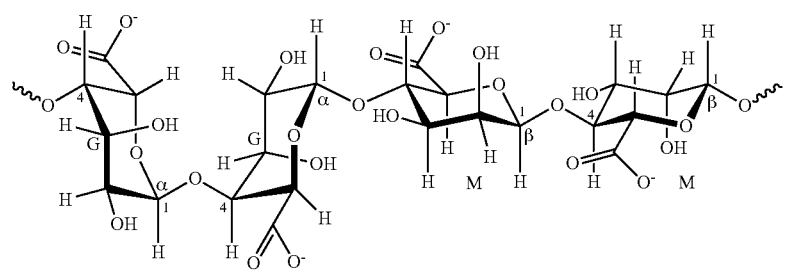

The residues are generally organized in blocks of identical or strictly alternating residues, e.g. MMMMMM . . . , GGGGGG . . . , or GMGMGM . . . .

The alginate polymers form, in the presence of monovalent cations, dissolvable solid particles. This is in clear contrast to the case, when the alginate polymers are instead in contact with divalent cations, such as $Ca^{2+}$. The divalent cations form links between different alginate polymers to thereby achieve cross-linking between the alginate polymers. The cross-linking in turn leads to the formation of an alginate film that is generally not dissolvable or at least difficult to dissolve in moist environments.

Suitable monovalent cations that can be used in the present embodiments include sodium ions ($Na^+$), potassium ions ($K^+$) and ammonium ions ($NH_4^+$), preferably $Na^+$.

Solid alginate particles can be formed from an aqueous solution of the alginate polymers in the presence of at least one monovalent cation. These solid particles form and lose acetate and derivates thereof, carboxymethyl cellulose, polycellulose ester, other cellulose derivates including ethylcellulose and propylcellulose, polyethylene, polypropylene, polystyrene, polyvinyl chloride, polyvinyl acetate, polymers of methacrylates and acrylates, natural rubber, polycarbonate, polyethylene terephtalate, polyester, polyamide and nylon.

In a preferred embodiment, the material of the semi-permeable pouch is not dissolvable or at least difficult to dissolve when being placed in the oral cavity of the subject. Thus, following administration of the biologically active substance enclosed by the alginate particles present in the pouch, the pouch with any remaining enclosed material is removed from the oral cavity and is discarded.

The pouch is semi-permeable implying that it comprises channels or pores allowing small particles with a diameter smaller than the pore size to freely transport from the inside of the pouch to the exterior, or indeed vice versa. However, larger particles present in the pouch and having a diameter larger than the pore size become entrapped therein.

The pores or channels of the semi-permeable pouch and the size of the multiple alginate particles are selected so that the particles, at least initially before being placed in the oral cavity, generally cannot pass through the semi-permeable membrane or net of the pouch. The solid particles can therefore preferably have an average diameter in the range from one or a few micrometers up to several millimeters, such as from 10 μm to 10 mm and preferably from 100 μm to 5 mm. Note that above given preferred ranges of the particle size is the average particle diameter. In practical implementations the individual alginate particles may have different diameters so that the multiple solid particles have distribution of particle diameters around the average diameter.

The permeability of the semi-permeable pouch, i.e. its nominal pore diameter, is therefore selected to be smaller than above mentioned preferred average particle diameter but is still large enough to allow the relevant biologically active substance to pass through the membrane or net of the pouch. As for the particle diameter, the pore size of the semi-permeable pouch is an average pore size with individual pore diameters distributed around this nominal pore size.

The solid particles can be formed using a single alginate type or a mixture of multiple, i.e. at least two, different alginate types. Generally, the dissolution rate of the of the alginate particles and thereby the release rate of the biologically active substance contained in the alginate matrix is dependent on the viscosity and the molecular weight of the alginate. In other words, the higher molecular weight and thereby the higher the viscosity of the alginate the longer dissolution rate upon contact with the moist mucous membrane in the oral cavity.

The molecular weight of the alginate can therefore be selected in order to achieve a desired controlled release of the biologically active substance. Thus, if a very quick release and uptake of the biologically active substance is desired, lower molecular weight alginates are used as compared to an application where an extended, slower release and uptake of the active substance is advantageous.

The smaller alginate molecules achieving a fast dissolution has generally an average molecular weight within a range from about 20 000 g/mol to about 90 000 g/mol, e.g. from 30 000 g/mol to 90 000 g/mol, including from 30 000 g/mol to 50 000 g/mol and from 30 000 g/mol to 40 000 g/mol. Such a low molecular weight alginate is sold under the trademark PROTANAL® LFR 5/60 by FMC BioPolymer. PROTANAL® LFR 5/60 has an average guluronic acid content of 65 to 75% and an average mannuronic acid content of 25 to 35%. This sodium alginate further has a viscosity of 300-700 mPas as measured in a 10% aqueous solution thereof at a temperature of 20° C. and at a shear rate of 20 rpm by use of a Brookfield viscometer with a spindle No. 2. Solid alginate particles made of, for instance, PROTANAL® LFR 5/60 can achieve a dissolution time of a few minutes, possible up to about 10 minutes, when the oral delivery product is being placed in the mouth of a human.

Correspondingly, a slower release is achieved with the high molecular weight alginates having a comparatively higher viscosity than the above-exemplified low molecular weight alginates. Such alginates can have an average molecular weight in the range from about 100 000 g/mol to about 500 000 g/mol, preferably from 100 000 g/mol to 250 000 g/mol, such as from 100 000 g/mol to 200 000 g/mol, preferably from 125 000 g/mol to 175 000 g/mol. A non-limiting example of a suitable alginate within these molecular weight ranges is PROTANAL® LF 10/60 marketed by FMC BioPolymer. PROTANAL® LF 10/60 is a sodium alginate having an average guluronic acid content of 40 to 45% and an average mannuronic acid content of 55 to 60%. The viscosity of the alginate is 20-70 mPas as measured in a 1% aqueous solution thereof at a temperature of 20° C. and at a shear rate of 20 rpm by use of a Brookfield viscometer with a spindle No. 2. Solid particles made of these high molecular weight alginates, such as PROTANAL® LF 10/60, and enclosed in the semi-permeable pouch has a dissolution time of several tens of minutes when being placed in the mouth of a human subject.

Generally the dissolution time of PROTANAL® LF 10/60 particles and therefore the uptake time of any active substance contained therein is 2-3 times longer than the dissolution time and uptake time achieved by PROTANAL® LF 5/60 particles.

A further suitable alginate that can be used in the embodiments includes PROTANAL® LF 120, a sodium alginate having an average guluronic acid content of 35 to 45% and an average mannuronic acid content of 55 to 65%. The viscosity of the alginate is 70-150 mPas as measured in a 1% aqueous solution thereof at a temperature of 20° C. and at a shear rate of 20 rpm by use of a Brookfield viscometer with a spindle No. 2. Generally the dissolution time of PROTANAL® LF 120 particles and therefore the uptake time of any active substance contained therein is 10-15 times longer than the dissolution time and uptake time achieved by PROTANAL® LF 5/60 particles.

It is anticipated by embodiments that a combination of multiple low molecular weight alginates, a combination of multiple high molecular weight alginates or a combination of at least one low molecular weight alginate and at least one high molecular weight alginate can be used in order to achieve a desired controlled dissolution profile. For instance and depending on the actual biologically active substance or substances enclosed in the alginate particles, a first set of the multiple alginate particles can be of a low molecular weight alginate to achieve a fast onset of the delivery of the biologically active substance. A second set of the multiple alginate particles are then instead made of a high molecular weight alginate to thereby achieve an extended and prolonged delivery of the biologically active substance. This may of course be extended even further by mixing more than two different types of alginates. Thus, by mixing alginates of varying molecular weights in different proportions different dissolution profiles and thereby different administration profiles can be achieved.

FIG. 7 is a diagram illustrating the serum concentration of a biologically active substance over time in a subject having an oral delivery product of the invention positioned in its oral cavity. The curve 40 illustrates the release of the biologically active substance from a low molecular weight alginate in the semi-permeable pouch, thereby achieving a resulting peak in serum concentration following a few minutes after the positioning of the oral delivery product in the oral cavity. The solid particles of a comparatively higher molecular weight alginate present a slower release of the biologically active substance, as is illustrated by the curve 42. The serum peak concentration due to those particles in the product may occur several tens of minutes later, such as 20-40 minutes after the insertion of the delivery product in the mouth. Curve 44 is the resulting serum concentration that is basically a sum of the two curves 40, 42. Thus, by mixing different alginate species a desired administration profile of a biologically active substance and desired serum concentration profile can be tailored.

This combined usage of solid particles of different alginate species can also be used for a combined delivery of multiple different biologically active substances in a single oral delivery product. Thus, a first biologically active substance is entrapped in the matrix of a first alginate species having a first average molecular weight. A second biologically active substance is then included in solid particles formed by a second alginate having a second average molecular weight. In such a case, following position of the oral delivery product in the mouth of the animal subject, the solid particles of the first alginate salt will dissolve more quickly than the particles of the second alginate. As a consequence, the first biologically active substance is first administered to the subject, while the delivery of the second active substance is delayed and more prolonged due to the higher dissolution time of the second alginate. This may of course be used for the case with more than two different biologically active substances and/or using at least two different alginate salt species for a given biologically active substance.

If substantially the same administration profile of two or more biologically active substances that are to be co-administered is desired, the biologically active substances can be included together in the alginate particles. However, if it is advantageous, such as from stability point of view, or that the biologically active substances require different local environments, such as pH, a first biologically active substance is included in a first set of solid particles of an alginate salt. A second biologically active substance is correspondingly included in the matrix of a second set of particles of the same alginate salt.

The at least one biologically active substance comprised within the matrix of the alginate salt particles can be any biologically active substance that can be entrapped in the particles and which is to be administered locally within the oral cavity or, preferably, systemically through uptake by the mucous membrane in the mouth. The oral delivery product is in particular advantageous in connection with sensitive substances susceptible to destruction or deterioration unless provided in a protected environment, requiring specific local environment for efficient delivery and/or cannot effectively be administered through other administration routes.

The alginate salt particles form an internal matrix, in which the local environment can be accurately controlled during the manufacture of the solid particles to achieve a desired matrix environment adapted for the particular biologically active substance. For instance, certain substances are prone to oxidize when present in an oxygen rich atmosphere. The alginates of the present embodiments effectively form an oxygen barrier thereby housing the sensitive substance in a low oxygen matrix, achieving a longer shelf life of the product without any need for compensating the oxidizing problem by adding more of the biologically active substance or requiring the addition of anti-oxidants.

Furthermore, some additives, such as color and flavoring agents, that are usually included in oral delivery products can be quite reactive. Such additives can be provided, in the oral delivery product external from the solid alginate particles, thereby being separate from the biologically active substance. Alternatively, the additives can be present in some of the alginate particles, while other alginate particles constitute the actual vehicles and carry the biologically active substance. However, even by providing these additives in a same aqueous solution as the biologically active substance and the alginate during production of the solid particles, the reactivity of the additives is strictly restricted once the alginate matrix is formed. Thus, even though additives and the biologically active substance are present within the same alginate particles, any deleterious reactions between the additives and the active substance are significantly reduced.

A controlled local matrix environment of the solid alginate particles can also be achieved by including selected molecules or agents in the aqueous solution during the production of the particles. For instance, the aqueous solution can be a buffered aqueous solution having a target acid, neutral or basic pH. When forming the solid particles, following drying, this buffer system will be entrapped within the alginate matrix together with the biologically active substance. This is particular advantageous if the biologically active substance will be decomposed or is in an inactive form unless present within a controlled pH interval. Furthermore, some biologically active substances can be very hard to take up by the subject body once released unless a certain pH interval is used. For instance, paracetamol or acetaminophen is very hard to dissolve in aqueous solutions unless a basic pH is used, sometimes requiring a pH of at least 11. A further example is nicotine, which requires a basic pH, such as between 8 and 9, for optimal uptake rate by the mucous membrane.

The solid alginate salt particles of the oral delivery product therefore preferably comprises a buffer system achieving a local pH that is selected to optimal or at least suitable in terms of stability, uptake and administration rate for the biologically active substance. Preferred examples of such buffer systems providing a basic pH include a phosphate buffer system, such as sodium phosphate, potassium phosphate; a carbonate buffer system, such as sodium carbonate, sodium bicarbonate, potassium carbonate, potassium bicarbonate; sodium hydroxide, potassium hydroxide, or any combination thereof.

The alginate particle matrices can also function as carrier matrix for biologically active substances having other particular requirements in terms of local environment. For instance, the anti-inflammatory drug diclofenac is traditionally administered embedded in a polyethylene glycol (PEG) aggregate as the diclofenac substance itself is really reactive and may otherwise irritate mucous membranes when administered orally. The alginate particles can, in their internal matrix, embed such PEG aggregates of diclofenac, thereby preserving the desired local PEG environment around the diclofenac molecules even in the alginate carrier.

The alginate particles of the oral delivery product of the invention can advantageously be used in connection with biologically active substances that are susceptible to destruction or deterioration in the gastrointestinal tract. Thus, by placing the oral delivery product in the oral cavity of a subject, the alginate particles will, due to the moist environment, start to dissolve and release the contained active substance. The active substance may then be taken up systemically through the mucous membrane in the mouth. Thus, an administration that avoids the first-pass metabolism of the biologically active substance is achieved.

The biologically active substance can be a therapeutic or non-therapeutic substance. Examples of the latter are biologically active ingredients that are not generally considered as a pharmaceutical, e.g. a naturopathic preparation. As an example of a non-pharmaceutical active ingredient a stimulant or a nutraceutical may be mentioned, the latter generally defined as a substance that may be considered a food or part of a food and provides medical or health benefits, including the prevention and treatment of disease. Other biologically active substances may have both a therapeutical and non-therapeutical use.

Therapeutically active substances are administered by the oral delivery product to treat or at least inhibit a disease or disorder against which the therapeutic substance is active. The substance and the oral delivery product may also be used for preventing a disease by being administered generally prior to any symptoms associated with the disease.

In order to illustrate how the oral delivery product may be used for various disorders, some non-limiting examples are given below:

The oral delivery product can be used to treat disorders in the stomach, where the substances are delivered from the "serum side" instead of from the gastric side or by uptake from the intestine and after liver passage. Typical disorders of the stomach would be the acid-related symptoms such as gastritis, ulcers, reflux or infections caused by *Helicobacter pylori*. The types of substances that can be used include antimicrobial agents, histamine-2-receptor antagonists and proton pump inhibitors. Because the oral delivery product can administer substances without the need to swallow water as with compressed tablets, the embodiments are very useful for any medication where the patients' disorder render them unable to swallow and/or retain the medication in the body. Typical disorders are stroke, migraine, acute cardiac conditions and patients with obstructed digestion channel, seasickness, nausea and other situations where water is not available or cannot be swallowed. Many different types of substances may be used, among these CNS-acting substances such as serotonin receptor antagonists, prescription-free sea-sickness tablets and various anti-inflammatory substances.

Another disorder where the oral delivery technology described herein can be used is obesity. Indeed, obese patients may be surgically treated (having parts of their stomach or the intestine removed) so as to reduce the absorption of substances from the gut. Delivery of medication by the oral delivery product that have their effects on the nervous system would be unaffected by the patents gastrointestinal operation history. An example of a type of substance that may be delivered in a film formulation according to the invention is sibutramin.

One interesting group of substances comprises the peptides and proteins. Substances of this group can not easily be taken in via the mouth and into the gut since they will be digested by enzymes, mainly proteases and peptidases, present both in the stomach and the intestine. However, peptides and certain proteins may be taken up trough mucous tissue after release from the oral delivery product since, in contrast to the gut, there is little peptidase activity in the mouth.

Since the drug-carrying alginate particles in the semi-permeable pouch and melting in the mouth, does not need to have any sugar additives and does not have to be swallowed it will be very suitable for oral diabetes therapy. Examples of suitable substance classes are the sulfoneurides, biguanid derivatives.

Patients that are very suitable candidates for delivery of substances according to the embodiments are the elderly people and children. Both these groups of patients are typically receiving more medication than the average and are often not able to self-medicate properly. Elderly people often get medication for sleep and for disorders typically associated with the ageing process such as dementia, Parkinson's disease, Alzheimer's disease, anxiety, depression and deficiencies of vitamins, nutrients and cofactors. The substance classes for this cohort of patients include CNS-acting drugs, antimicrobial agents and low molecular-weight cofactors.

Further examples of biologically active substances that can be administered alone or in combinations by the oral delivery product include urinary incontinence agents, e.g. oxybutynin; antihistamines, e.g. dimenhydrinate, diphenhydramine, chlorpheniramine, dexchlorpheniramine maleate; analgesics, e.g. aspirin, codeine morphine, dihyromorphone, oxycodone, etc.; anti-inflammatory agents, e.g. naproxyn, diclofenac, indomethacin, ibuprofen, acetaminophen, aspirin, sulindac; gastrointenstinals and antiemetics, e.g. metoclopramide; anti-epileptics, e.g. phenytoin, meprobamate, nitrezepam; vadosidaltors, e.g. nifedipine, papaverine, diltiazem, nicardirine; antitussive agents and expectorants, e.g. codein phosphate; anti-asthmatics, e.g. theophylline; antispasmodics, e.g. atropine, scopolamine; hormones, e.g. insulin; diuretics; e.g. eltacrymic acid bendrofluazide; antihypotensives, e.g. propranolol, clonidine; bronchodilators, e.g. albuterol, anti-inflammatory steroids, e.g. hydrocortisone, triamcinolone, prednisone; antibiotics, e.g. tetracycline, antihemmorrhoidals; anitdiarrheals; mucolytics; sedatives; decongestants; laxatives; antacids, etc.

The oral delivery product is in particular suitable for comprising a nicotine (3-(1-methyl-2-pyrrolidinyl)pyridine) substance as biologically active substance. This includes synthetic nicotine and nicotine extracts from tobacco plants, such as the genus *Nicotiana*, nicotine base, nicotine hydrochloride, nicotine dihydrochloride, nicotine monotartrate, nicotine bitartrate, nicotine sulphate, nicotine zinc chloride (monohydrate) and nicotine salicylate. Furthermore, other alkaloids with the same direction of activity including nornicotine and lobeline, e.g. of the species *Lobeliaceae* and *Lobelia*, methylanabasine, anabasine can alternative be used.

In addition to being used in smoking curing, the oral delivery product comprising nicotine as biologically active substance can be used as a substitute for wet snuff mainly seen today in the U.S. and Scandinavia. Although wet snuff is generally not implicated in the cardiovascular and lung disease morbidity and mortality caused by smoking, the content of nitrosamines in snuff poses a potential hazard for some cancer diseases. It is therefore of interest to make available to consumers a snuff-like product while minimizing this potential hazard.

The oral delivery product comprising the multiple solid alginate particles with nicotine in the semi-permeable pouch effectively meets the above mentioned objectives. The product has the further advantage that it can use the same semi-permeable pouch material and size that is traditionally used in pre-baked snuff pouches or bags. Thus, the physical feeling the snuffer gets when placing the oral delivery product under the lip is substantially the same as when placing a snuff pouch.

The oral delivery product comprising nicotine as biologically active agent has further advantages when being used instead of a traditional tobacco-containing snuff product. Alginates have scientifically proven properties in promoting wound healing, and soothing and alleviating skin irritations. People regularly using snuff products have an increased risk of irritation to the mucous membranes under the lip, possibly even leading to open wounds. Using the oral delivery agent of the invention, the alginates dissolving from the alginate particles will promote wound healing and soothe the irritations caused by the prior art snuff products.

Further examples of active substances that can be used according to the embodiments include caffeine, vitamin B12, vitamin C, vitamin E, Bioperine® (extract from the fruit of *Piper Nigrum* L or *Piper longum* L and contains a high percentage of piperine), Coenzyme Q10, selenium, glutathione, alpha lipoic acid (ALA), folic acid, ginseng, antioxidants, minerals, paracetamol and acetylsalicylic acid.

The alginate particles may also, in particular when the active substance is nicotine, comprise tobacco, typically a small amount of tobacco added for providing a desired flavour that mimics the one of traditional snuff products.

FIG. 1A is a view from above of an example of an oral delivery product 1 according to an embodiment. The oral delivery product comprises the semi-permeable pouch 10 filled with the alginate particles 20. In the figure, the reference number 14 indicates a pore or channel of the pouch 10, allowing passage of the biologically active substance, such as nicotine, through the pouch wall or net. The pouch 10 is generally sealed in the short ends 12 thereof, entrapping the alginate particles 20 in the formed pouch chamber. Sealing can be used according to various techniques, which are all well-known today within the snuff pouch producing industry. A non-limiting example of sealing technique is heat sealing. FIG. 1B is a side view of the oral delivery product 1.

The solid particles of the alginate salt may comprise up to 85% by weight of the total formulation of the at least one biologically active substance, such as up to 70% by weight, or up to 60% by weight, such as 5 to 60% by weight, preferably 5 to 50% by weight, or 10 to 40% by weight. It should however be understood that it is also contemplated that the alginate formulation may contain very low levels of the biologically active substance, if this for any reason is desired, e.g. if the active substance is to be delivered at a very small dosage. Thus, if preferably, the alginate particles may contain the at least one biologically active substance at a very low level, e.g. as low as 0.000001% by weight.

The semi-permeable pouch may also, in addition to the alginate particles, comprise excipients or additives, such as filler particles of a filler material. An example of suitable filler material is cellulose, such as microcrystalline cellulose. Such microcrystalline cellulose can form particles having varying particle diameters. In such a case, the above-suggested diameter ranges for the alginate particles are also of relevance for the microcrystalline cellulose particles. AVICEL® PH-200 is an example of a microcrystalline cellulose having a suitable average particle size of 180 μm diameter. Other cellulose particles can be selected from AVICEL® PH-100, PH-102, PH-103, PH-105, PH-112, PH-113, PH-300, PH-302, VIVACEL® grades 101, 102, 12, 20 and EMOCEL® grades 50M and 90M and mixtures thereof.

With reference to FIG. 2, in a typical embodiment the semi-permeable pouch 10 encloses from about 1 to 100% by weight of the alginate particles 20 and 0 to 99% by weight of the filler particles 30, preferably 5 to 75% by weight of the alginate particles 20 and 25 to 95% by weight of the filler particles 30, such as 5 to 50% by weight of the alginate particles 20 and 50 to 95% by weight of the filler particles 30, and more preferably 10 to 30% by weight of the alginate particles 20 and 70 to 90% by weight of the filler particles 30.

The optional filler material can be used as passive filler material or may indeed be used as an additional substance carrier. In the latter case, the at least one biologically active substance enclosed by the alginate particles 20 and/or another biologically active substance can be sorbed onto the surface of the filler particles 30. Microcrystalline cellulose particles 30 are generally highly porous particles 30 with a large part thereof being voids and pores. In such a case, the biologically active substance, such as nicotine, can be absorbed or adsorbed to the cellulose surface in the many voids and pores, thereby achieving a very large sorbtion surface. WO 2007/104573 discloses such microcrystalline cellulose particles 30 with sorbed nicotine. The teaching of that patent document as far as relating to nicotine-carrying cellulose particles 30 is hereby incorporated by reference for usage as an active filler material. Such active filler materials carrying a biologically surface, can be used to achieve a very fast onset of the substance delivery that can occur before or at least partly overlapping the delivery from light molecular weight alginate particles 20.

A further example of additive that can be used in the oral delivery product is at least one plasticizer, preferably comprised in the solid particles of the alginate salt of monovalent cation. The plasticizer, when present, may be selected from e.g. polyethylene glycols, glycerol and sorbitol. A preferred plasticizer is sorbitol optionally together with a small part of glycerol. A suitable amount of plasticizer is e.g. from 1 to 85 g, such as from 5 to 70 g or from 10 to 70 g, e.g. from 30 to 70 g, or from 40 to 70 g, including from 50 to 60 g of plasticizer per 100 g of alginate.

Further physiologically, i.e. non-toxic at the added level, and/or pharmacologically acceptable additives include one or more flavouring agents, such as taste maskers, and/or colouring agents. Examples of flavouring agents are essential oils including distillations, solvent extractions or cold expressions of chopped flowers, leaves, peel or pulped whole fruit comprising mixtures of alcohols, esters, aldehydes and lactones. Essences including either diluted solutions of essential oils or mixtures of synthetic chemical blends to match the desired flavour of the fruit, e.g. strawberry, raspberry, cranberry, orange, lemon, lime, cherry and black current can also be used. Further examples include artificial and natural flavours of brews and liquors, e.g. cognac, whiskey, rum, gin, sherry, port, and wine; tobacco, coffee, tea, cacao, mint, peppermint, eucalyptus, liquorice, and menthol.

Sweeteners, such as sorbitol, xylitol, maltitol, isomalt, aspartame, acesulfame, saccharin, sucrose, glucose, fructose, lactose, mannitol, etc., can also or in addition be added to the gum.

According to an embodiment colouring additives can be selected from dyes containing chemical groups which absorb light including dyes, such as tartrazine, indigo carmine, amaranth, erythrosine, carbon black, titanium dioxide and any mixtures thereof.

The sweeteners, flavouring and colouring agents, if included, may be present from about 0.075% w/w to about 35% w/w, such as from about 0.075% w/w to about 5% w/w.

Even though generally not necessary for the storage and efficient delivery of the biologically active substance from the oral delivery product, further additives selected from binders, wetting agents, stabilizing agents, surface active agents, absorption enhancers, texture-improving agents and anti-oxidant may optionally be included in the oral delivery product, preferably by being comprised in the matrix defined by the alginate salt of monovalent cation.

FIG. 3 is a flow diagram illustrating an embodiment of producing an oral delivery product according to an embodiment. The method generally starts in step S1, which forms multiple solid particles from an aqueous solution of at least one alginate salt of monovalent cation and at least one biologically active substance. The at least one active substance is further contained within the matrices of the multiple particles formed by the at least one alginate salt. A next step S2 fills a semi-permeable pouch designed for being placed in the oral cavity of an animal subject, preferably human subject and more preferably under the lip of the human subject, with the formed solid alginate particles. The so filled pouch is then enclosed and sealed thereby obtaining the oral delivery product.

If any filler particles are to be used, they are of course filled in the semi-permeable pouch prior to the sealing thereof.

FIG. 4 is a flow diagram illustrating additional steps of the producing method in FIG. 3. The method starts in step S10, where the at least one alginate salt of monovalent cation is added to an aqueous solution, preferably a buffered aqueous solution of the at least one biologically active substance. In an alternative embodiment, the biologically active substance is instead added to an, preferably buffered, aqueous solution of the at least one alginate salt.

Any additives, such as plasticizers, flavoring agents, coloring agents, are preferably added to the solution prior to the addition of the alginate salt, though a subsequent addition of the additives is indeed feasible.

A next step S11 stirs the mixture to form a homogenous solution. Optionally mild heating, such as up to 60° C., preferably no more than up to 50° C. or 40° C., may be applied during the stirring operation. The method then continues to step S1 of FIG. 3.

FIG. 5 is a flow diagram illustrating an embodiment of the particle forming step S1 in FIG. 3. In this embodiment, the solid alginate particles are formed by subjecting the (buffered) aqueous solution to a freeze granulation process. Generally, the freeze granulation process is a two-step process. The first step S20 involves spray freezing the aqueous alginate and substance solution into a cooling liquid, such as liquid $N_2$, to form frozen granulates. The frozen alginate granulates of with the biologically active substance are then subject to freeze drying, such as at a temperature of about −10° C. to −60° C., such as about −40° C., to form the multiple solid alginate particles carrying the biologically active substance in their matrices.

Freeze granulation has several production advantages, such as allowing formation of a wide range of particle diameters and providing tight control of the granule density. Furthermore, the mild drying provides a low degree of oxidation and is therefore suitable for substances sensitive for oxidation.

Appliances for performing freeze granulation, even in a large-scale, are today available on the market, such as from PowderPro Göteborg AB.

If multiple different alginate particles are to be used they may all be mixed in the same aqueous solution so that the solid particles formed by the freeze granulation processes are a mixture of the alginate molecules. Alternatively, multiple separate aqueous solutions comprising different alginates or different alginate mixtures can individually be subject to the freeze granulation. In such a case, solid alginate particles of different alginate species are obtained.

FIG. 6 is a flow diagram illustrating another embodiment of forming the solid alginate particles in step S1 of FIG. 3. The method continues from step S11 of FIG. 4. A next step S30 dries the aqueous solution comprising the alginate salt, the at least one biologically active substance, preferably the buffering agent or agents and optionally other additives and excipients. Drying is preferably performed at room temperature, e.g. 17-25° C., and under a normal atmosphere for a time period required to form one or more solid bodies. Drying may also be performed under a dry atmosphere or under a lower than atmospheric pressure in order to speed up the drying process. In the case the biologically active substance is not susceptible to thermal degradation, drying may be further accelerated by raising the temperature, such as to about 35° C. Drying may also be accelerated by distributing the solution onto a solid surface and allowing to dry into a solid body.

The one or more solid bodies formed following the drying process in step S30 is then cut or ground into small solid alginate particles having a desired particle size. An optional sorting process can be conducted by sorting the formed alginate particles based on particle diameter in different meshes. The method then continues to step S2, where the alginate particles are packet in the pouch.

If multiple alginate species are to be used, a first implementation runs the method in steps S30-S31 individually for each alginate (mixture) solved in its dedicated aqueous solution. The resulting solid particles are then mixed together prior before being filled in the pouch. In a second implementation, a single aqueous solution comprises a mixture of different alginates are formed, dried and then cut into small solid particles.

EXAMPLES

Example 1

A buffered aqueous solution comprising paracetamol as active pharmaceutical ingredient can be made with the following ingredients:

| | |
|---|---|
| 10 g | sodium alginate corresponding to PROTANAL ® LFR 5/60; |
| 80 g | distilled water; |
| 3 g | sorbitol; |
| 2 g | glycerol; |
| 2 g | cranberry extract; |
| 1 drop | green food colour; |
| | sodium hydroxide; |
| 5 g | paracetamol. |

The active pharmaceutical ingredient is mixed with water and the pH adjusted to about 8-8.5 by addition of aqueous NaOH. The plasticizers, flavouring and colouring agents are added. The PROTANAL® LFR 5/60 is then added to the above-mentioned aqueous solution at room temperature in small portions and mixed until a homogenous solution is obtained.

The solution is allowed to dry at room temperature at atmospheric pressure until a sold is formed. The solid is ground into small alginate particles having an average diameter size of 200-500 μm.

Example 2

The proceeding generally as in EXAMPLE 1, alginate particles are prepared by the use of the following ingredients:

| | |
|---|---|
| 12 g | sodium alginate corresponding to PROTANAL ® LFR 5/60; |
| 80 g | distilled water; |
| 3 g | sorbitol; |
| 2 g | glycerol; |
| 2 g | cranberry extract; |
| 1 drop | green food colour; |
| | sodium hydroxide; |
| 12 g | paracetamol. |

Example 3

An alginate formulation is prepared by use of the following ingredients:

| | |
|---|---|
| 12 g | sodium alginate corresponding to PROTANAL ® LFR 5/60; |
| 80 g | distilled water; |
| 3 g | sorbitol; |
| 2 g | glycerol; |
| 2 g | cranberry extract; |
| 1 drop | green food colour; |
| 6 g | ibuprofen dissolved in ethanol. |

The active pharmaceutical ingredient, ibuprofen, is dissolved in a small volume of ethanol and the solution is mixed with water, resulting in precipitation of ibuprofen crystals. The plasticizers, flavouring and colouring agents are added. PROTANAL® LFR 5/60 is then added, at room temperature in small portions and mixed until a homogenous milky white suspension of ibuprofen crystals is obtained. The suspension is dried at room temperature at atmospheric pressure, giving a solid that can be cut or ground into solid particles of a target size distribution.

Example 4

Proceeding generally as in EXAMPLE 1, but using aqueous bicarbonate buffer to regulate the pH of the composition:

| | |
|---|---|
| 12 g | sodium alginate corresponding to PROTANAL ® LFR 5/60; |
| 80 g | aqueous sodium bicarbonate buffer pH 8-8.5; |
| 3 g | sorbitol; |
| 2 g | glycerol; |
| 2 g | cranberry extract; |
| 1 drop | green food colour; |
| 5 g | acetylsalicylic acid. |

Example 5

Proceeding generally as in EXAMPLE 1, a formulation is prepared by use of the following ingredients:

| | |
|---|---|
| 12 g | sodium alginate corresponding to PROTANAL ® LFR 5/60; |
| 80 g | distilled water; |
| 2 g | cranberry extract; |
| | sodium hydroxide; |
| 12 g | paracetamol. |

Example 6

An alginate formulation is prepared by use of the following ingredients:

| | |
|---|---|
| 11 g | sodium alginate corresponding to PROTANAL ® LFR 5/60; |
| 80 g | aqueous potassium phosphate buffer pH 8.5, 0.1M; |
| 2 g | glycerol; |
| 3 g | sorbitol; |
| 5.5 g | nicotine bitartrate. |

The active ingredient, nicotine bitartrate, is mixed with the buffer. Glycerol and sorbitol are added. The PRONATAL® LFR 5/60 is then added to the thus prepared aqueous solution at room temperature in small portions and mixed until a homogenous solution is obtained.

The solution is allowed to dry at room temperature at atmospheric pressure.

Example 7

An alginate formulation is prepared by use of the following ingredients:

| | |
|---|---|
| 10 g | sodium alginate corresponding to PROTANAL ® LF 10/60; |
| 150 g | aqueous potassium phosphate buffer pH 8.5, 0.1M; |
| 2 g | glycerol; |
| 3 g | sorbitol; |
| 5.5 g | nicotine bitartrate. |

The active ingredient, nicotine bitartrate, is mixed with the buffer. Glycerol and sorbitol are added. The PRONATAL® LF 10/60 is then added to the thus prepared aqueous solution at room temperature in small portions and mixed until a homogenous solution is obtained.

The solution is allowed to dry at room temperature at atmospheric pressure.

Example 8

An alginate formulation is prepared by use of the following ingredients:

| | |
|---|---|
| 6 g | sodium alginate corresponding to PROTANAL ® LFR 5/60; |
| 4 g | sodium alginate corresponding to PROTANAL ® LF 10/60; |
| 150 g | aqueous potassium phosphate buffer pH 8.5, 0.1M; |
| 2 g | glycerol; |
| 3 g | sorbitol; |
| 5.5 g | nicotine bitartrate. |

The active ingredient, nicotine bitartrate, is mixed with the buffer. Glycerol and sorbitol are added. The PRONATAL® LFR 5/60 and LF 10/60 are then added to the thus prepared aqueous solution at room temperature in small portions and mixed until a homogenous solution is obtained.

The solution is allowed to dry at room temperature at atmospheric pressure.

Example 9

The proceeding generally as in EXAMPLE 1, alginate particles are prepared by the use of the following ingredients:

| | |
|---|---|
| 10 g | sodium alginate corresponding to PROTANAL ® LFR 5/60; |
| 80 g | distilled water; |
| 4 g | sorbitol; |
| 3 g | glycerol; |
| 4 g | 1% (w/w) powder of vitamin B12 - the reminder being tablet filler material. |

The alginate particles formed according to any of the above listed examples are then filled in a semi-permeable pouch that is being sealed, preferably by heat sealing, to form an oral delivery product.

Filling of the pouch with the particle and sealing thereof can be conducted using conventional techniques, e.g. used in the snuff industry today.

It will be understood by a person skilled in the art that various modifications and changes may be made to the present invention without departure from the scope thereof, which is defined by the appended claims.

The invention claimed is:

1. An oral delivery product comprising:
    a semi-permeable pouch designed for placement in an oral cavity of a subject; and
    multiple solid particles of at least one alginate salt of monovalent cation, wherein said multiple solid particles (i) comprise at least one biologically active substance within a matrix formed by said at least one alginate salt of monovalent cation, (ii) have an average diameter in a range of from 100 μm to 5 mm, (iii) are dissolvable in the moist environment of the oral cavity, and (iv) are enclosed in said semi-permeable pouch.

2. The product according to claim 1, further comprising filler particles of a filler material.

3. The product according to claim 2, wherein said filler particles are microcrystalline cellulose particles.

4. The product according to claim 3, wherein said microcrystalline cellulose particles have sorbed an amount of said at least one biologically active substance in voids and pores within said microcrystalline cellulose.

5. The product according to claim 2, wherein said semi-permeable pouch encloses 10 to 30% by weight of said multiple solid particles and 70 to 90% by weight of said filler particles.

6. The product according to claim 1, wherein said multiple solid particles of said at least one alginate salt of monovalent cation further comprise at least one plasticizer.

7. The product according to claim 1, wherein said multiple solid particles of said at least one alginate salt of monovalent cation further comprise a buffer system within said matrix.

8. The product according to claim 7, wherein said buffer system provides a basic pH to said multiple solid particles and is selected from a phosphate buffer system or a carbonate buffer system.

9. The product according to claim 1, wherein said monovalent cation is selected from $Na^+$, $K^+$ and $NH_4^+$.

10. The product according to claim 1, wherein said multiple solid particles of said at least one alginate salt of monovalent cation comprise said at least one biologically active substance at a level of from 0.000001 to 85% by weight of a total weight of said multiple solid particles.

11. The product according to claim 1, wherein said at least one biologically active substance is nicotine.

12. The product according to claim 1, wherein said multiple solid particles of said at least one alginate salt of monovalent cation comprise:
    a first set of multiple solid particles of a first alginate salt of monovalent cation comprising said at least one biologically active substance within a matrix formed by said first alginate salt of monovalent cation, said first alginate salt having a first average molecular weight; and
    a second set of multiple solid particles of a second alginate salt of monovalent cation comprising said at least one biologically active substance within a matrix formed by said second alginate salt of monovalent cation, said second alginate salt having a second average molecular weight that is comparatively larger than said first average molecular weight.

13. The product according to claim 12, wherein said first average molecular weight is within a first range of from 30,000 g/mol to 90,000 g/mol and said second average molecular weight is within a second range of from 100,000 g/mol to 500,000 g/mol.

14. The product according to claim 12, wherein said first alginate salt is an alginate salt of monovalent cation having a guluronic acid content of 65 mole % to 75 mole % and a mannuronic acid content of 25 mole % to 35 mole % and a 10% aqueous solution thereof at a temperature of 20° C. has a viscosity of 300-700 mPas as measured at a shear rate of 20 rpm by use of a Brookfield viscometer with a spindle No. 2.

15. The product according to claim 12, wherein said second alginate salt is an alginate salt of monovalent cation having a guluronic acid content of 40 mole % to 45 mole % and a mannuronic acid content of 55 mole % to 60 mole % and a 1% aqueous solution thereof at a temperature of 20° C. has a viscosity of 20-70 mPas as measured at a shear rate of 20 rpm by use of a Brookfield viscometer with a spindle No. 2.

16. The product according to claim 12, wherein the first alginate salt of monovalent cation and the second alginate salt of monovalent cation have different rates of dissolution in the moist environment of the oral cavity.

17. A method of producing an oral delivery product according to claim 1, comprising:
    forming multiple solid particles from an aqueous solution of at least one alginate salt of monovalent cation and at least one biologically active substance, wherein said at least one biologically active substance is contained within a matrix formed by said at least one alginate salt of monovalent cation; and
    enclosing said multiple solid particles in a semi-permeable pouch designed for placement in an oral cavity of a subject,
    wherein said multiple solid particles have an average diameter in a range of from 100 μm to 5 mm.

18. The method according to claim 17, wherein said aqueous solution is formed by:
    adding said at least one alginate salt of monovalent cation to an aqueous solution of said at least one biologically active substance; and
    stirring said mixture until a homogenous solution is obtained.

19. The method according to claim 17, wherein said forming step comprises subjecting said aqueous solution to a freeze granulation process to form said multiple solid particles.

20. The method according to claim 19, wherein said freeze granulation process comprises:
    spray freezing said aqueous solution into a cooling liquid to form said multiple solid particles; and
    freeze drying said multiple solid particles.

21. The method according to claim 17, wherein said forming step comprises:
    drying said aqueous solution of said at least one alginate salt of monovalent cation and said at least one biologically active substance to form a solid body; and
    cutting said multiple solid particles from said solid body.

22. The method according to claim 21, wherein said drying step comprises:
    drying a first aqueous solution of a first alginate salt of monovalent cation and said at least one biologically active substance to form a first solid body with said at least one biologically active substance contained within a matrix formed by said first alginate salt of monovalent cation, said first alginate salt having a first average molecular weight; and
    drying a second aqueous solution of a second alginate salt of monovalent cation and said at least one biologically active substance to form a second body with said at least one biologically active substance contained within a matrix formed by said second alginate salt of monovalent cation, said second alginate salt having a second average molecular weight that is comparatively larger than said first average molecular weight, said cutting step comprises:

cutting a first set of multiple solid particles from said first solid body; and cutting a second set of multiple solid particles from said second solid body, and said enclosing step comprises enclosing said multiple solid particles of said first set and of said second set in said semi-permeable pouch.

23. The method according to claim 21, wherein said drying step comprises drying an aqueous solution of a first alginate salt of monovalent cation having a first average molecular weight, a second alginate salt of monovalent cation having a second average molecular weight that is comparatively larger than said first average molecular weight, and said at least one biologically active substance to form a solid body with said at least one biologically active substance contained within a matrix formed by said first and second alginate salt of monovalent cation.

24. A method of inhibiting or preventing a disease comprising positioning, in an oral cavity of a subject suffering from said disease, an oral delivery product according to claim 1 and comprising a semi-permeable pouch designed for placement in said oral cavity and enclosing multiple solid particle of at least one alginate salt of monovalent cation, said multiple solid particles comprising at least one pharmaceutically active substance within a matrix formed by said at least one alginate salt of monovalent cation, said pharmaceutically active substance being capable of inhibiting or preventing said disease, and said multiple solid particles having an average diameter in a range of from 100 µm to 5 mm.

* * * * *

UNITED STATES PATENT AND TRADEMARK OFFICE
CERTIFICATE OF CORRECTION

PATENT NO. : 9,925,145 B2
APPLICATION NO. : 13/255980
DATED : March 27, 2018
INVENTOR(S) : Fredrik Hübinette et al.

Page 1 of 1

It is certified that error appears in the above-identified patent and that said Letters Patent is hereby corrected as shown below:

On the Title Page

Item (30) "Foreign Application Priority Data", change "0950153" to --0950153-7--.

Signed and Sealed this
Twelfth Day of June, 2018

Andrei Iancu
*Director of the United States Patent and Trademark Office*